United States Patent
Chen

(10) Patent No.: US 8,736,142 B2
(45) Date of Patent: *May 27, 2014

(54) POLARITY SWITCHING CIRCUIT

(75) Inventor: Shih-Chang Chen, Hsinchu (TW)

(73) Assignee: Microjet Technology Co., Ltd., Hsinchu (TW)

( * ) Notice: Subject to any disclaimer, the term of this patent is extended or adjusted under 35 U.S.C. 154(b) by 2 days.

This patent is subject to a terminal disclaimer.

(21) Appl. No.: 13/568,565

(22) Filed: Aug. 7, 2012

(65) Prior Publication Data

US 2013/0043765 A1    Feb. 21, 2013

(30) Foreign Application Priority Data

Aug. 15, 2011 (TW) .............................. 100129104 A
Jul. 2, 2012 (TW) .............................. 101123704 A

(51) Int. Cl.
    *H02M 7/5395* (2006.01)
(52) U.S. Cl.
    USPC ........................................... 310/317; 363/41
(58) Field of Classification Search
    USPC ........... 363/41, 95, 97, 131; 310/316.01, 317, 310/318
    See application file for complete search history.

(56) References Cited

U.S. PATENT DOCUMENTS

| | | | | |
|---|---|---|---|---|
| 4,507,762 | A * | 3/1985 | Meyer et al. | 310/317 |
| 6,177,753 | B1 * | 1/2001 | Atsuta | 310/316.01 |
| 2006/0113865 | A1 * | 6/2006 | Yoshida | 310/317 |
| 2006/0261704 | A1 * | 11/2006 | Battaglin et al. | 310/317 |
| 2007/0242427 | A1 * | 10/2007 | Yamamoto et al. | 310/318 |
| 2010/0301701 | A1 * | 12/2010 | Chen et al. | 310/317 |

* cited by examiner

*Primary Examiner* — Gary L Laxton
*Assistant Examiner* — Alex Torres-Rivera
(74) *Attorney, Agent, or Firm* — Kirton McConkie; Evan R. Witt

(57) ABSTRACT

A polarity switching circuit includes: a first current-limiting resistor and a second current-limiting resistor connected to a DC high voltage; a first transistor switch, a second transistor switch, a fourth transistor switch, and a fifth transistor switch respectively controlled by a first PWM signal and a second PWM signal; a third transistor and a sixth transistor switch whose control terminals are respectively connected to the first transistor switch and the fourth transistor switch; a first filter connected to the second transistor switch and the third transistor switch and a contact of a piezoelectric actuator; and a second filter connected to the fifth transistor switch and the sixth transistor switch and another contact of the piezoelectric actuator. When the first and the second PWM signal are switching between a high level and a low level, output AC voltages with smoothed AC waveforms are supplied to the contacts of the piezoelectric actuator.

7 Claims, 13 Drawing Sheets

POLARITY SWITCHING CIRCUIT

FIELD OF THE INVENTION

The invention is related to a polarity switching circuit, and more particularly to a polarity switching circuit for outputting an output AC voltage with a smooth waveform to drive a piezoelectric actuator.

BACKGROUND OF THE INVENTION

With the progress of technology, various electronic products have been developed for stimulating the growth of the information technology market. Undoubtedly, such trend will carry on. Also, with the advancement of the microelectronic technology, the electronic products will be more versatile and more miniaturized. Besides, the portability of the electronic products will be enhanced as well. Nowadays, the user can handle all kinds of business easily with various electronic products. In recent years, the so-called piezoelectric actuator have been developed and applied to electronic products. The piezoelectric actuator have the advantages of low voltage, high immunity to noise, small size, fast response, low heat radiation, high sophistication, high conversion efficiency, and high controllability.

The piezoelectric actuator generally requires an AC voltage that is applied thereto to drive the piezoelectric actuator to carry out high-speed periodically operations. Hence, the piezoelectric actuator needs a driving system to operate. The driving system is used to convert a DC voltage into an AC voltage for driving the piezoelectric actuator. Referring to FIG. 1, the conventional driving system 1 is used to convert a DC input voltage $V_{DC}$ into output AC voltages $V_{o1}$ and $V_{o2}$ for driving a piezoelectric actuator 9 shown in FIG. 2A. The driving system 1 includes a boost circuit 10, a voltage multiplier 11, and a polarity switching circuit 12. The boost circuit 10 is connected to the DC input voltage $V_{DC}$ to convert the DC input voltage $V_{DC}$ into a transient voltage $V_T$ by the switching operations of the internal switch elements and the energy storage and filtering operations carried out by the internal inductors, capacitors, and diodes. The voltage multiplier 11 is connected to the transient voltage $V_T$ to multiply the transient voltage $V_T$ by 4 to generate a DC high voltage $V_B$. The polarity switching circuit 12 is used to convert the DC high voltage $V_B$ into output AC voltages $V_{o1}$ and $V_{o2}$ for driving the piezoelectric actuator 9.

Referring to FIGS. 2A, 2B, and 3 with reference to FIG. 1, in which FIG. 2A shows the internal circuitry of the polarity switching circuit of FIG. 1 and FIG. 2B illustrates the operation of the polarity switching circuit of FIG. 1 as the digital signal $f_{sw}$ is low. Also, FIG. 3 shows the timing of the voltage signals of FIG. 2A and FIG. 2B. The polarity switching circuit 12 is connected to the DC high voltage $V_B$, the input DC low voltage $V_{in}$, and the digital signal $f_{sw}$ to convert the DC high voltage $V_B$ into output AC voltages $V_{o1}$ and $V_{o2}$ driving the piezoelectric actuator 9 to operate repetitively. The polarity switching circuit 12 includes a first current-limiting resistor R21, a second current-limiting resistor R22, a third current-limiting resistor R23, a first transistor switch Q21, a second transistor switch Q22, a third transistor switch Q23, a fourth transistor switch Q24, a fifth transistor switch Q25, a sixth transistor switch Q26, and a seventh transistor switch Q27.

As the digital signal $f_{sw}$ is high and is sent to the control terminal of the first transistor switch Q21 and the control terminal of the sixth transistor switch Q26, the first transistor switch Q21 and the sixth transistor switch Q26 that are connected to the ground terminal G will turn on. As the first current-limiting resistor R21 is connected to the first transistor switch Q21, the circuit branch consisted of the first current-limiting resistor R21 will be connected to the ground terminal G. Meanwhile, the second transistor switch Q22 and the fourth transistor switch Q24 will turn off as the control terminal of the second transistor switch Q22 and the control terminal of the fourth transistor switch Q24 are connected to the circuit branch consisted of the first current-limiting resistor R21, thereby driving the voltage level of the circuit branch consisted of the second current-limiting resistor R22 to a high level due to the DC high voltage $V_B$, hence, the third transistor switch Q23 will turn on as the control terminal of the third transistor switch Q23 is connected to the circuit branch consisted of the second current-limiting resistor R22. Meanwhile, the control terminal of the seventh transistor switch Q27 is connected to the digital signal $f_{sw}$ with a high level. Therefore, the seventh transistor switch Q27 is also turned on. As the third current-limiting resistor R23 is connected to the seventh transistor switch Q27, the circuit branch consisted of the third current-limiting resistor R23 is connected to the ground terminal G. Also, the control terminal of the fifth transistor switch Q25 is connected to the circuit branch consisted of the third current-limiting resistor R23, the fifth transistor switch Q25 is turned off. Therefore, the current will flow in the direction as indicated by the arrows shown in FIG. 2A.

As the digital signal $f_{sw}$ is low, as shown in FIG. 2B, the operations of all the transistor switches are reverse to the operations of all the transistor switches indicated in FIG. 2A. Under this condition, the current flow will be indicated by the arrows shown in FIG. 2B. In this manner, the output AC voltages $V_{o1}$ and $V_{o2}$ of the polarity switching circuit 12 will have a square waveform on the piezoelectric actuator 9, as indicated by the waveform of the voltage signal of $(V_{o1}-V_{o2})$ shown in FIG. 3.

As the output AC voltages $V_{o1}$ and $V_{o2}$ of the polarity switching circuit 12 have square waveforms on the piezoelectric actuator 9, the piezoelectric actuator 9 is rapidly charged as the voltage levels of the output AC voltages $V_{o1}$ and $V_{o2}$ are bobbing rapidly. Although the piezoelectric actuator 9 can reach the peak of its amplitude due to the rapid charging of the piezoelectric actuator 9, the power loss is increased as well. More disadvantageously, as the polarity switching circuit 12 is configured to charge the piezoelectric actuator 9 rapidly with square AC waves, the piezoelectric actuator 9 will vibrate under a natural resonant frequency. Such vibration will cause tremendous noise.

Hence, it is needed to develop a polarity switching circuit to address the problems encountered by the prior art. The invention can meet this need.

THE SUMMARY OF THE INVENTION

An object of the invention is to provide a polarity switching circuit for addressing the problems of the huge power loss and the tremendous noise generated during the operation phase of the piezoelectric actuator.

To this end, the invention provides a polarity switching circuit for converting a DC high voltage into an output AC voltage for driving a piezoelectric actuator. The inventive polarity switching circuit includes a first current-limiting resistor connected to the DC high voltage; a second current-limiting resistor connected to the DC high voltage; a first transistor switch having a control terminal connected to a first pulse-width modulating (PWM) signal, a current input terminal connected to the first current-limiting resistor and the DC high voltage, and a current output terminal connected to a ground terminal; a second transistor switch having a control terminal connected to the first pulse-width modulating signal, a current input terminal, and a current output terminal connected to the ground terminal; a third transistor switch having a control terminal connected to the current input terminal of the first transistor switch and the first current-limiting resistor, a current input terminal connected to the DC high voltage, and a current output terminal connected to the current input terminal of the second transistor switch; a fourth transistor switch having a control terminal connected to a second pulse-width modulating signal, a current input terminal connected to the DC high voltage through the second current-limiting resistor, and a current output terminal connected to the ground terminal; a fifth transistor switch having a control terminal connected to the second pulse-width modulating signal, a current input terminal, and a current output terminal connected to the ground terminal; a sixth transistor switch having a control terminal connected to the current input terminal of the fourth transistor switch and the second current-limiting resistor, a current input terminal connected to the DC high voltage, and a current output terminal connected to the current input terminal of the fifth transistor switch; a first filter connected to the current input terminal of the second transistor switch, the current output terminal of the third transistor switch, a first contact of the piezoelectric actuator, and the ground terminal; and a second filter connected to the current input terminal of the fifth transistor switch, the current output terminal of the sixth transistor switch, a second contact of the piezoelectric actuator, and the ground terminal. When the first pulse-width modulating signal and the second pulse-width modulating signal are alternately and respectively switching between a high level and a low level, the first filter and the second filter are configured to filter the output AC voltage into a smoothed AC waveform, thereby providing an output AC voltage with a smoothed waveform for the piezoelectric actuator.

Another aspect of the invention is attained by the provision of a polarity switching circuit for converting a DC high voltage into an output AC voltage for driving a piezoelectric actuator. The inventive polarity switching circuit includes a first pulse-width modulating signal; a second pulse-width modulating signal; a first filter for receiving a pulse voltage generated by converting the DC high voltage and connected to a first contact of the piezoelectric actuator; and a second filter for receiving another pulse voltage generated by converting the DC high voltage and connected to a second contact of the piezoelectric actuator. When the first pulse-width modulating signal and the second pulse-width modulating signal are alternately and respectively switching between a high level and a low level, the first filter and the second filter are configured to filter the output AC voltage into a smoothed AC waveform, thereby providing an output AC voltage with a smoothed waveform for the piezoelectric actuator.

Now the foregoing and other features and advantages of the invention will be best understood through the following descriptions with reference to the accompanying drawings, in which:

DESCRIPTION OF THE PREFERRED EMBODIMENT

Several exemplary embodiments embodying the features and advantages of the invention will be expounded in following paragraphs of descriptions. It is to be realized that the present invention is allowed to have various modification in different respects, all of which are without departing from the scope of the present invention, and the description herein and the drawings are to be taken as illustrative in nature, but not to be taken as a confinement for the invention.

Figure 1:
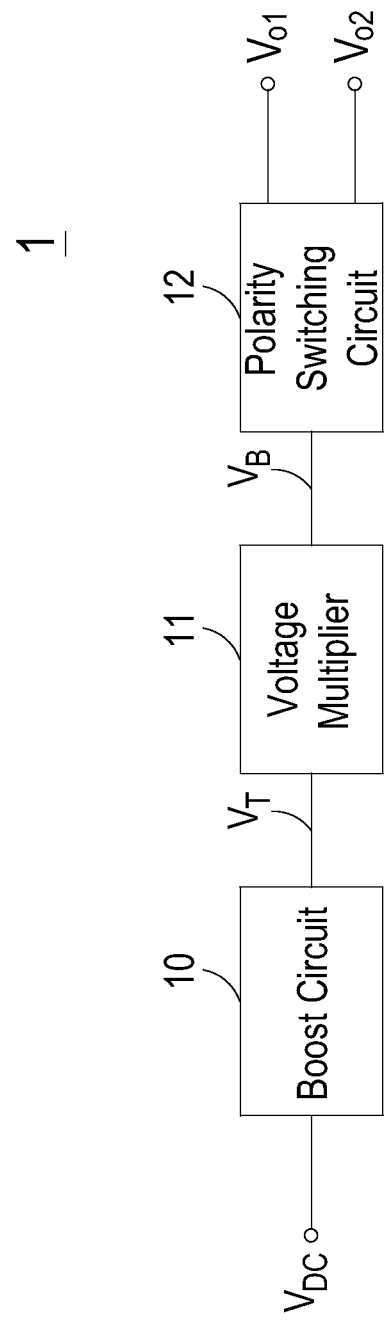
FIG. 1 is a circuit block diagram showing the driving system for piezoelectric actuator according to the prior art.
Figure 4A:
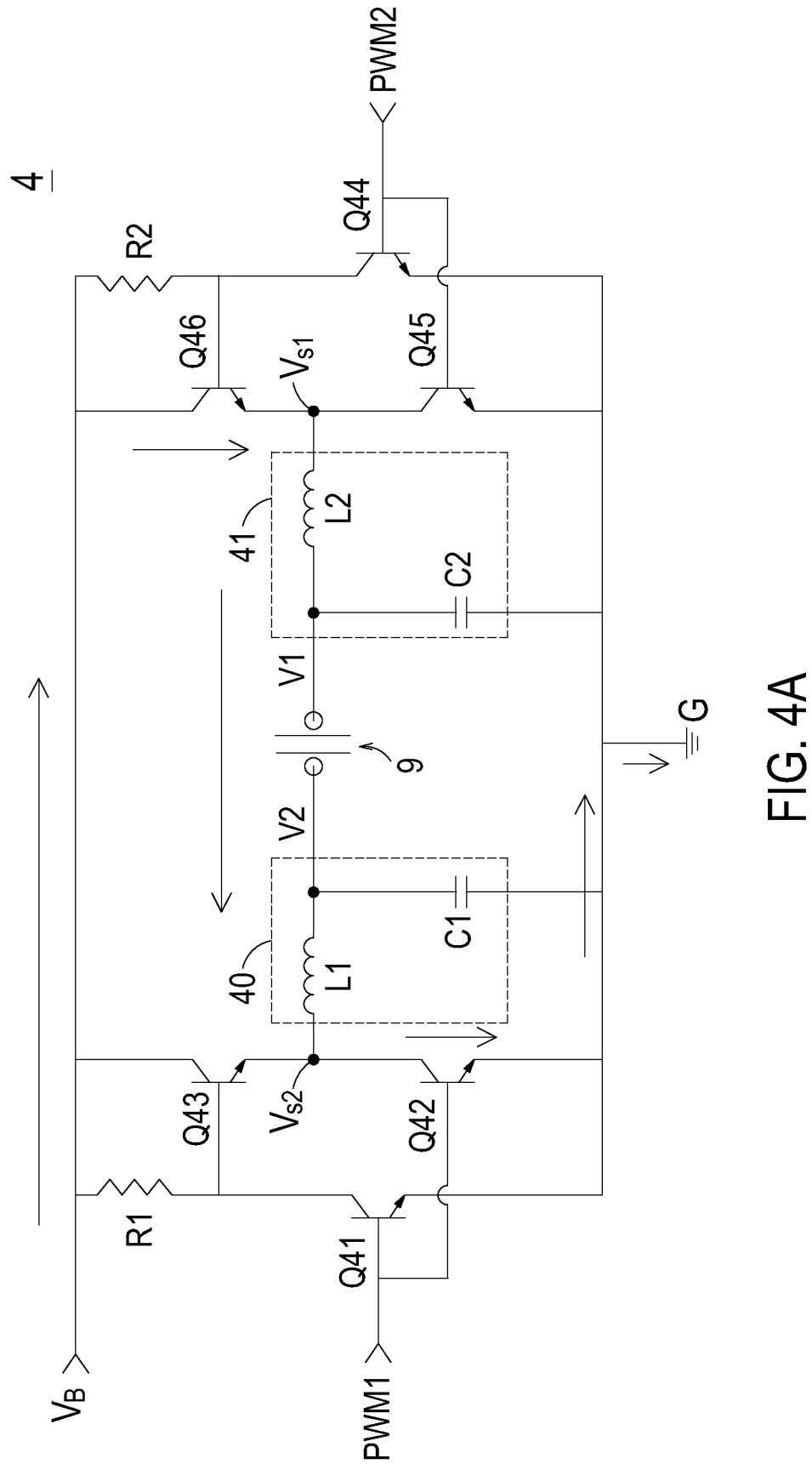
FIG. 4A shows the internal circuitry of the polarity switching circuit according to a preferred embodiment of the invention.
Figure 4B:
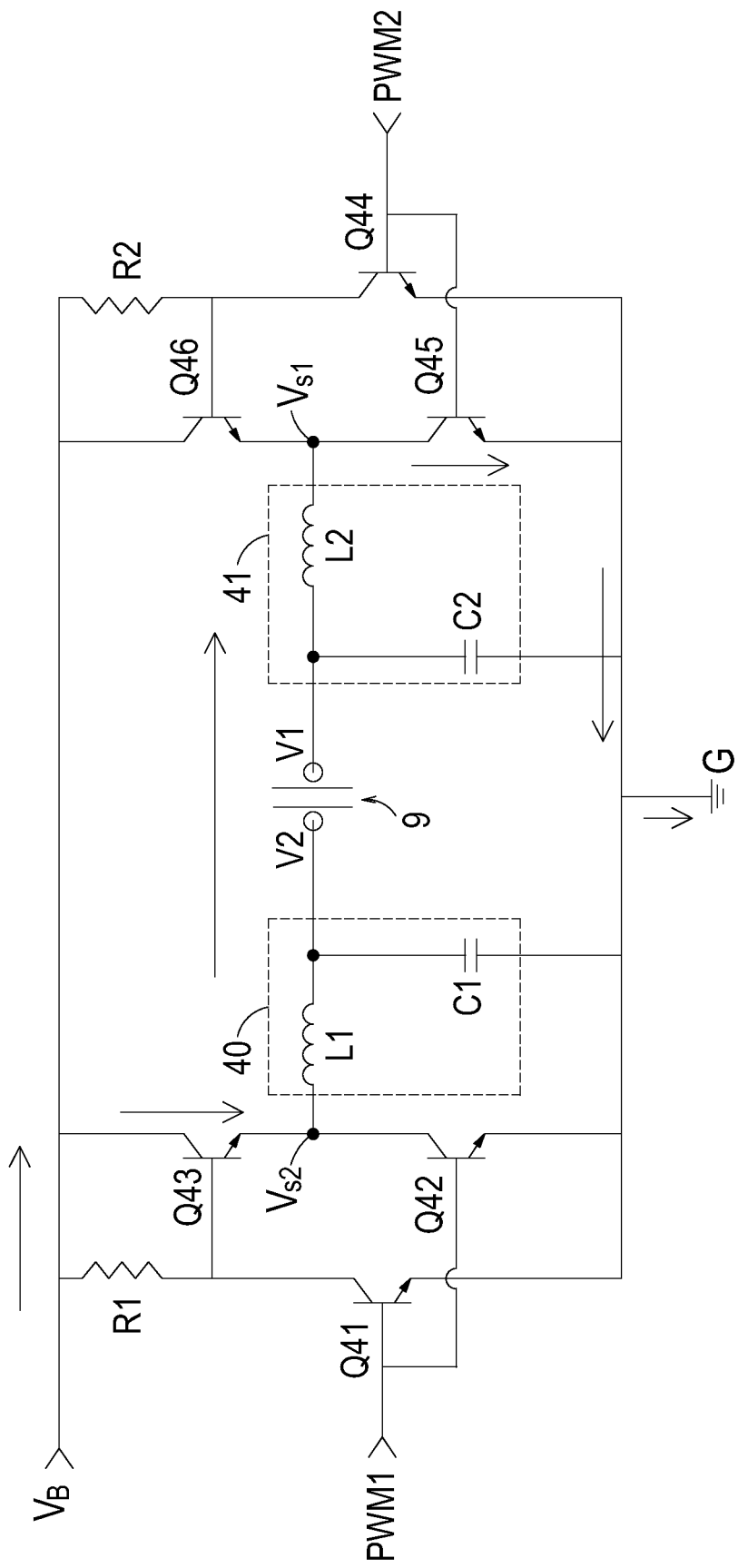
FIG. 4B illustrates the circuit operation of the polarity switching circuit of FIG. 4A as the first pulse-width modulating signal PWM1 is low and the second pulse-width modulating signal PWM2 is switching between a low level and a high level.

Referring to FIG. 4A and FIG. 4B, in which FIG. 4A shows the internal circuitry of the polarity switching circuit according to a preferred embodiment of the invention, and FIG. 4B illustrates the circuit operation of the polarity switching circuit of FIG. 4A as the first pulse-width modulating signal PWM1 is low and the second pulse-width modulating signal PWM2 is switching between a low level and a high level. As shown in FIG. 4A and FIG. 4B, the polarity switching circuit 4 is connected to a DC high voltage $V_B$ and is configured to convert the DC high voltage $V_B$ into output AC voltages $V_1$ and $V_2$ according to a first pulse-width modulating signal PWM1 and a second pulse-width modulating signal PWM2, thereby driving a piezoelectric actuator to operate repetitively. The DC high voltage $V_B$ is outputted from a voltage multiplier 11 shown in FIG. 1. The polarity switching circuit 4 includes a first transistor switch Q41, a second transistor switch Q42, a third transistor switch Q43, a fourth transistor switch Q44, a fifth transistor switch Q45, a sixth transistor switch Q46, a first filter 40, a second filter 41, a first current-limiting resistor R1, and a second current-limiting resistor R2.

The first current-limiting resistor R1 is connected to the DC high voltage $V_B$, and is connected to a current input terminal of the first transistor switch Q41 and a control terminal of the third transistor switch Q43. The second current-limiting resistor R2 is connected to the DC high voltage $V_B$, and is connected to a current input terminal of the fourth transistor switch Q44 and a control terminal of the sixth transistor switch Q46.

A control terminal of the first transistor switch Q41 is connected to the first pulse-width modulating signal PWM1. A current input terminal of the first transistor switch Q41 is connected to the DC high voltage $V_B$ through the first current-limiting resistor R1. A current output terminal of the first transistor switch Q41 is connected to a ground terminal G. A control terminal of the second transistor switch Q42 is connected to the first pulse-width modulating signal PWM1. A current input terminal of the second transistor switch Q42 is connected to the first filter 40. A current output terminal of the second transistor switch Q42 is connected to the ground terminal G. A control terminal of the third transistor switch Q43 is connected to the current input terminal of the first transistor switch Q41. A current input terminal of the third transistor switch Q43 is connected to the DC high voltage $V_B$. A current output terminal of the third transistor switch Q43 is connected to the first filter 40 and the current input terminal of the second transistor switch Q42. The first filter 40 is connected to a contact of the piezoelectric actuator 9 and the ground terminal G.

Figure 5A:
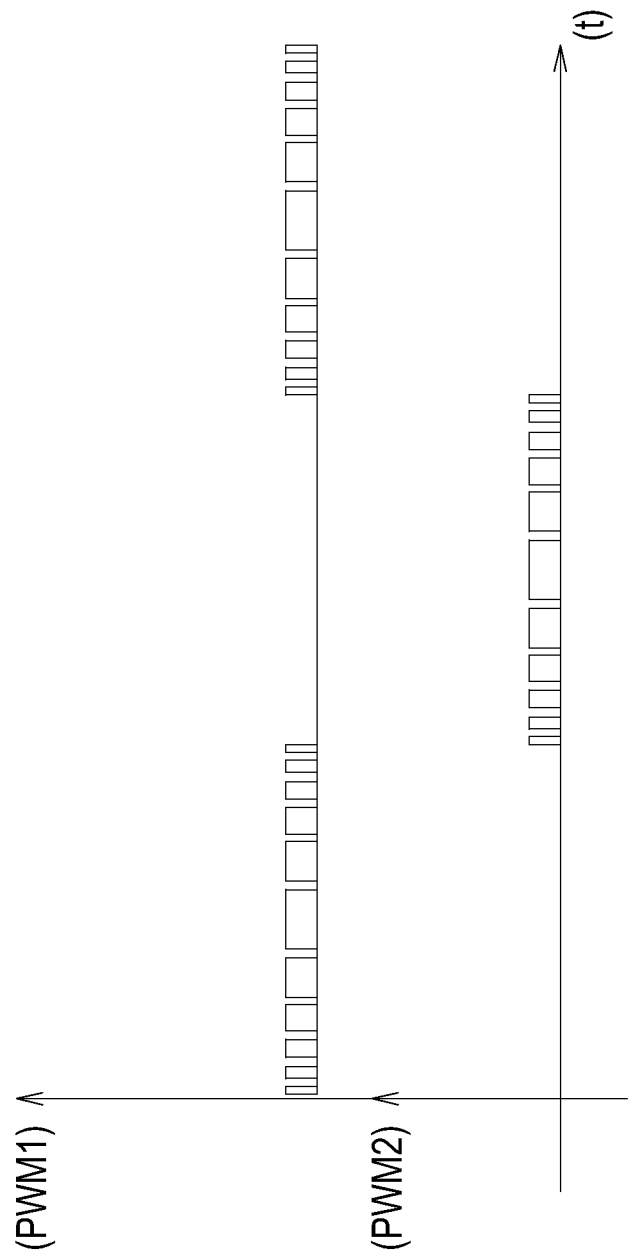
FIG. 5A-FIG. 5C are the timing diagrams of the voltage signals of FIG. 4A and FIG. 4B.
Figure 5B:
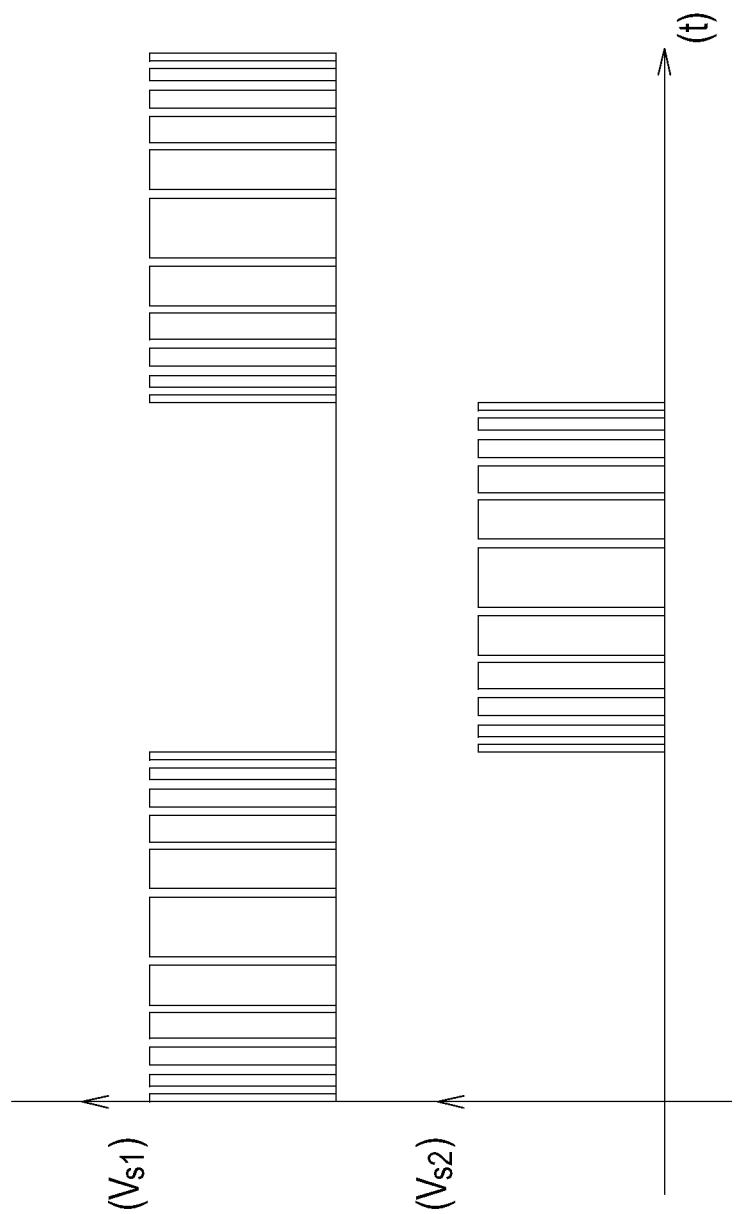
Figure 5C:
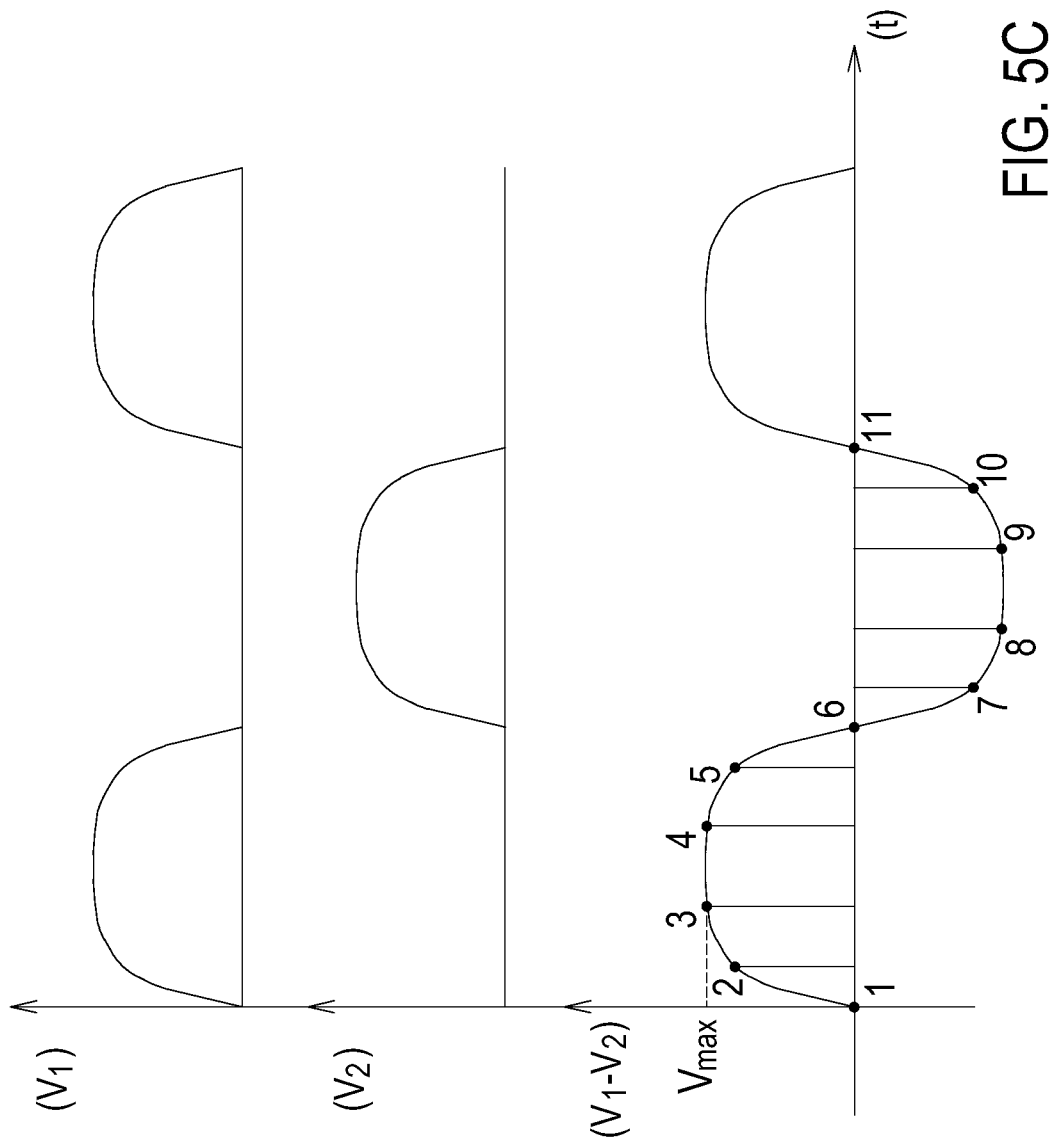

A control terminal of the fourth transistor switch Q44 is connected to a second pulse-width modulating signal PWM2. A current input terminal of the fourth transistor switch Q44 is connected to the DC high voltage $V_B$ through the second current-limiting resistor R2. A current output terminal of the fourth transistor switch Q44 is connected to the ground terminal G. A control terminal of the fifth transistor switch Q45 is connected to the second pulse-width modulating signal PWM2. A current input terminal of the fifth transistor switch Q45 is connected to the second filter 41. A current output terminal of the of the fifth transistor switch Q45 is connected to the ground terminal G. A control terminal of the sixth transistor switch Q46 is connected to the current input terminal of the fourth transistor switch Q44. A current input terminal of the sixth transistor switch Q46 is connected to the DC high voltage $V_B$. A current output terminal of the sixth transistor switch Q46 is connected to the second filter 41 and the current input terminal of the fifth transistor switch Q45. The second filter 41 is connected to another contact of the piezoelectric actuator 9 and the ground terminal G. Referring to FIG. 5A, FIG. 5B, and FIG. 5C with reference to FIG. 4A and FIG. 4B, in which FIG. 5A, FIG. 5B, and FIG. 5C are the timing diagrams of the voltage signals of FIG. 4A and FIG. 4B, respectively. As shown in FIG. 4A, FIG. 4B, FIG. 5A, FIG. 5B, and FIG. 5C, the first pulse-width modulating signal PWM1 and the second pulse-width modulating signal PWM2 are alternately switched between the high level and the low level. That is, when the first pulse-width modulating signal PWM1 is switching between the high level and the low level, the second pulse-width modulating signal PWM2 is low. On the contrary, when the second pulse-width modulating signal PWM2 is switching between the high level and the low level, the first pulse-width modulating signal PWM1 is low.

When the first pulse-width modulating signal PWM1 is switching between the high level and the low level and the second pulse-width modulating signal PWM2 is low, the low level of the second pulse-width modulating signal PWM2 will force the fourth transistor switch Q44 and the fifth transistor switch Q45 to turn off. Also, the sixth transistor switch Q46 will turn on as its control terminal is connected to the DC high voltage $V_B$. Meanwhile, the high-frequency switching of the first pulse-width modulating signal PWM1 between the high level and the low level will drive the first transistor switch Q41, the second transistor switch Q42, and the third transistor switch Q43 to switch synchronously. That is, when the first transistor switch Q41 and the second transistor switch Q42 are turned on, the third transistor switch Q43 is turned off. On the contrary, when the first transistor switch Q41 and the second transistor switch Q42 are turned off, the third transistor switch Q43 is turned on. Therefore, when first transistor switch Q41 and the second transistor switch Q42 are turned on, the current will flow in the direction indicated by the arrows shown in FIG. 4A.

On the contrary, when the second pulse-width modulating signal PWM2 is switching between the high level and the low level and the first pulse-width modulating signal PWM1 is low, the operations of the transistor switched are reversed. That is, the low level of the first pulse-width modulating signal PWM1 will force the first transistor switch Q41 and the second transistor switch Q42 to turn off, and the third transistor switch Q43 will turn on as its control terminal is connected to the DC high voltage $V_B$. Meanwhile, the high-frequency switching of the second pulse-width modulating signal PWM2 between the high level and the low level will drive the fourth transistor switch Q44, the fifth transistor switch Q45, and the sixth transistor switch Q46 to switch synchronously. That is, when the fourth transistor switch Q44 and the fifth transistor switch Q45 are turned on, the sixth transistor switch Q46 is turned off. On the contrary, when the fourth transistor switch Q44 and the fifth transistor switch Q45 are turned off, the sixth transistor switch Q46 is turned on. Therefore, when fourth transistor switch Q44 and the fifth transistor switch Q45 are turned on, the current will flow in the direction indicated by the arrows shown in FIG. 4B.

Hence, when the timing of the first pulse-width modulating signal PWM1 and the timing of the second pulse-width modulating signal PWM2 are set as indicated in FIG. 5A, that is, the frequency of the first pulse-width modulating signal PWM1 and the frequency of the second pulse-width modulating signal PWM2 are respectively drifting from a high value to a low value and then to a high value, the first pulse-width modulating signal PWM1 and the second pulse-width modulating signal PWM2 will enable the polarity switching circuit 4 to convert the DC high voltage $V_B$. Under this condition, a second switching voltage $V_{s2}$ is generated between the current input terminal of the second transistor switch Q42 and the current output terminal of the third transistor switch Q43, and a first switching voltage $V_{s1}$ is generated between the current input terminal of the fifth transistor switch Q45 and current output terminal of the sixth transistor switch Q46. Also, as shown in FIG. 5B, the first switching voltage $V_{s1}$ and the second switching voltage $V_{s2}$ that are pulse voltages will drift in synchronization with the first pulse-width modulating signal PWM1 and the second pulse-width modulating signal PWM2 from a high-frequency band to a low-frequency band and then to a high-frequency band. The first switching voltage $V_{s1}$ and the second switching voltage $V_{s2}$ will be filtered by the second filter 41 and the first filter 40, respectively, thereby generating output AC voltages $V_1$ and $V_2$ with smoothed AC waveforms, as shown in FIG. 5C.

Referring to FIG. 5C, the driving electric energy applying to the piezoelectric actuator 9, that is, the remainder of the output AC voltage $V_1$ and the output AC voltage $V_2$, will reach a first fractional value of the maximum voltage $V_{max}$ linearly within a first time period after the polarity switching circuit 4 starts operating, as indicated by the curve between the numerical marking 1 and the numerical marking 2. Afterwards, the waveform of the driving electric energy applying to the piezoelectric actuator 9 will smoothly bob up and reach the maximum voltage $V_{max}$ within a first predetermined time period, as indicated by the curve between the numerical marking 2 and the numerical marking 3. Afterwards, the waveform of the driving electric energy applying to the piezoelectric actuator 9 will be remain flat within a second time period, as indicated by the curve between the numerical marking 3 and the numerical marking 4. Afterwards, the waveform of the driving electric energy applying to the piezoelectric actuator 9 will smoothly decline and reach a second fractional value of the maximum voltage $V_{max}$ linearly within a second predetermined time period, as indicated by the curve between the numerical marking 4 and the numerical marking 5. Finally, the waveform of the driving electric energy applying to the piezoelectric actuator 9 will drop to zero linearly, as indicated by the curve between the numerical marking 5 and the numerical marking 6. As to the waveform of the driving electric energy applying to the piezoelectric actuator 9 indicated by the curve between the numerical marking 6 and the numerical marking 11, it is not intended to elaborate as the characteristics of this segment of waveform are similar to those of the segment of waveform indicated by the curve between the numerical marking 1 and the numerical marking 6. Also, the rising rate, the falling rate, the knee point radian, and the maintaining time of the maximum voltage $V_{max}$ of the smooth AC waveform of the output AC voltages $V_1$ and $V_2$ of the polarity switching circuit 4 can be tuned by adjusting the pulse width of the first pulse-width modulating signal PWM1 and the second pulse-width modulating signal PWM2.

Figure 2A:
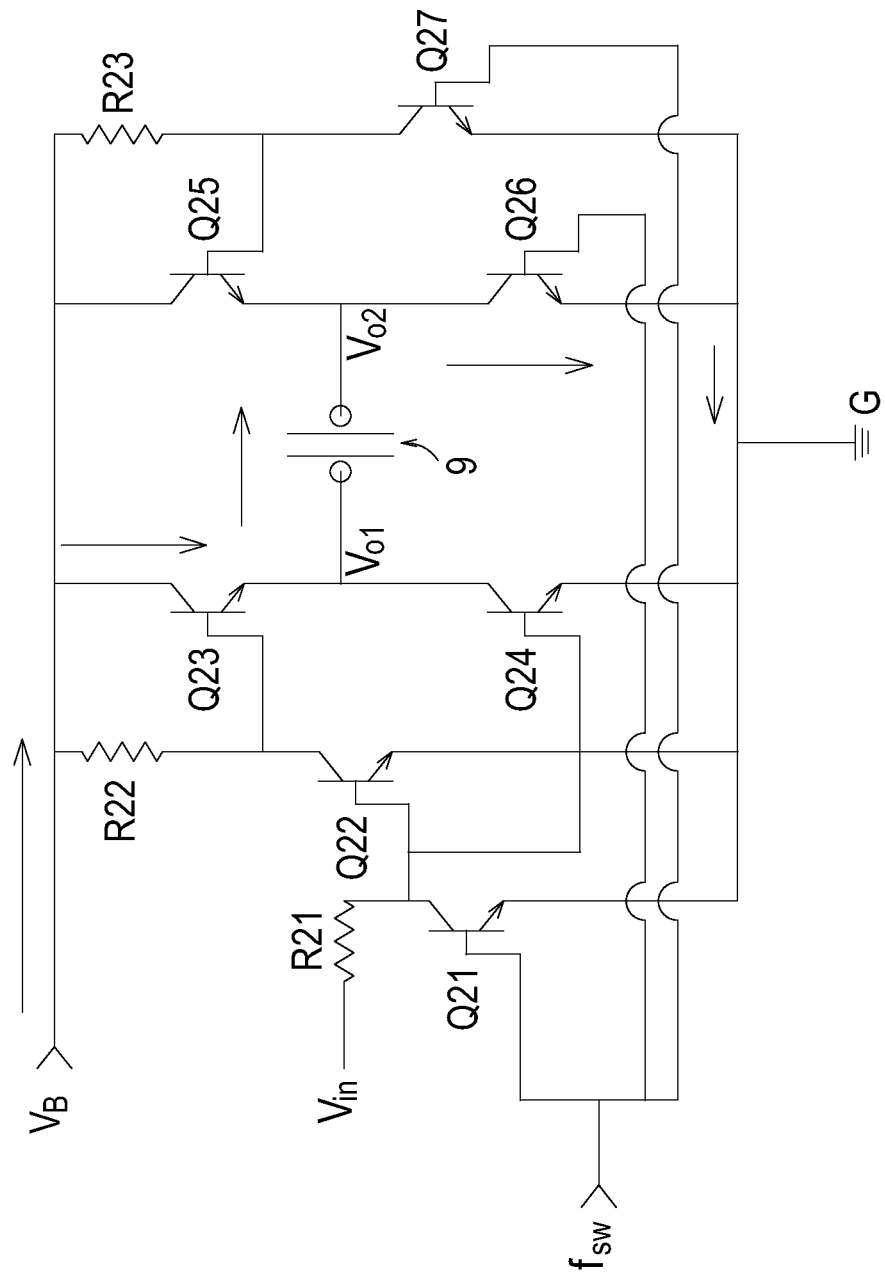
FIG. 2A shows the internal circuitry of the polarity switching circuit of FIG. 1.
Figure 2B:
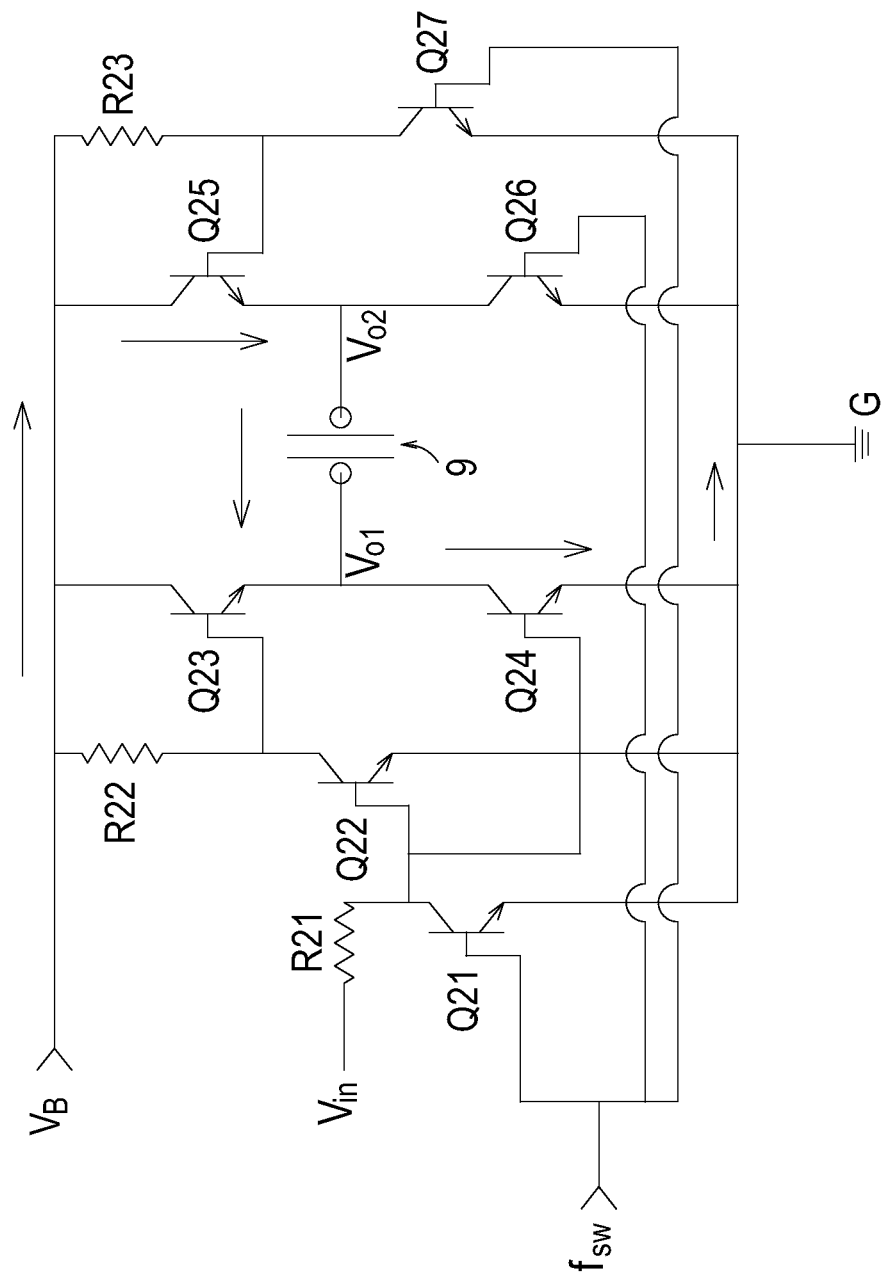
FIG. 2B illustrates the operation of the polarity switching circuit of FIG. 1 as the digital signal $f_{sw}$ is low.
Figure 3:
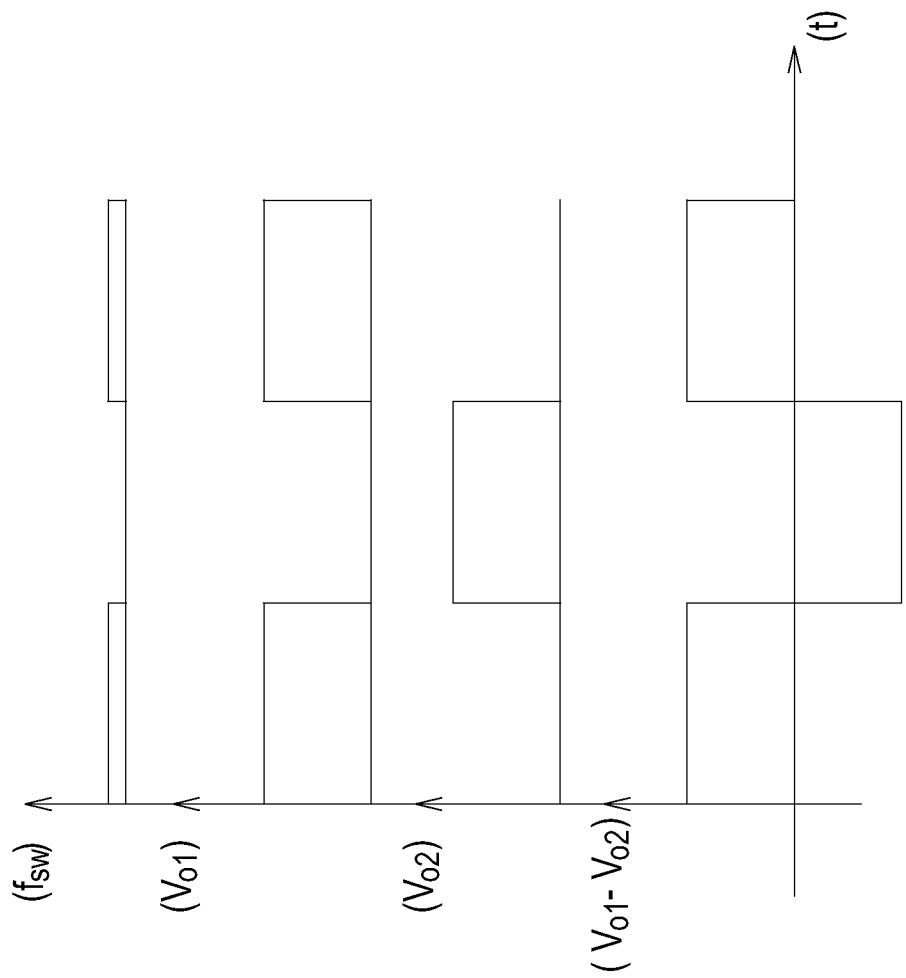
FIG. 3 shows the timing of the voltage signals of FIG. 2A and FIG. 2B.

The output AC voltages $V_1$ and $V_2$ of the polarity switching circuit 4 have smooth AC waveforms and are applied to the two contacts of the piezoelectric actuator 9. According to the prior art as shown in FIG. 2A, the output AC voltages $V_{o1}$ and $V_{o2}$ of the conventional polarity switching circuit have square AC waveforms and are applied to the piezoelectric actuator 9. Thus, the inventive polarity switching circuit can charge the piezoelectric actuator 9 moderately, which would reduce the power loss as a result of rapid charging. More advantageously, the vibrations of the piezoelectric actuator 9 under a natural resonant frequency can be suppressed, thereby avoiding the noise generated during the operation phase of the piezoelectric actuator 9.

In alternative embodiments, the first filter 40 can include a first inductor $L_1$ and a first capacitor $C_1$, as shown in FIG. 4A. In FIG. 4A, the first inductor $L_1$ is connected to the piezoelectric actuator 9, the current input terminal of the second transistor switch Q42, and the current output terminal of the third transistor switch Q43. The first capacitor $C_1$ is connected to the piezoelectric actuator 9, the first inductor $L_1$, and the ground terminal G. The second filter 41 can include a second inductor $L_2$ and a second capacitor $C_2$. The second inductor $L_2$ is connected to the piezoelectric actuator 9, the current input terminal of the fifth transistor switch Q45, and the current output terminal of the sixth transistor switch Q46. The second capacitor $C_2$ is connected to the piezoelectric actuator 9, the second inductor $L_2$, and the ground terminal G.

Figure 6:
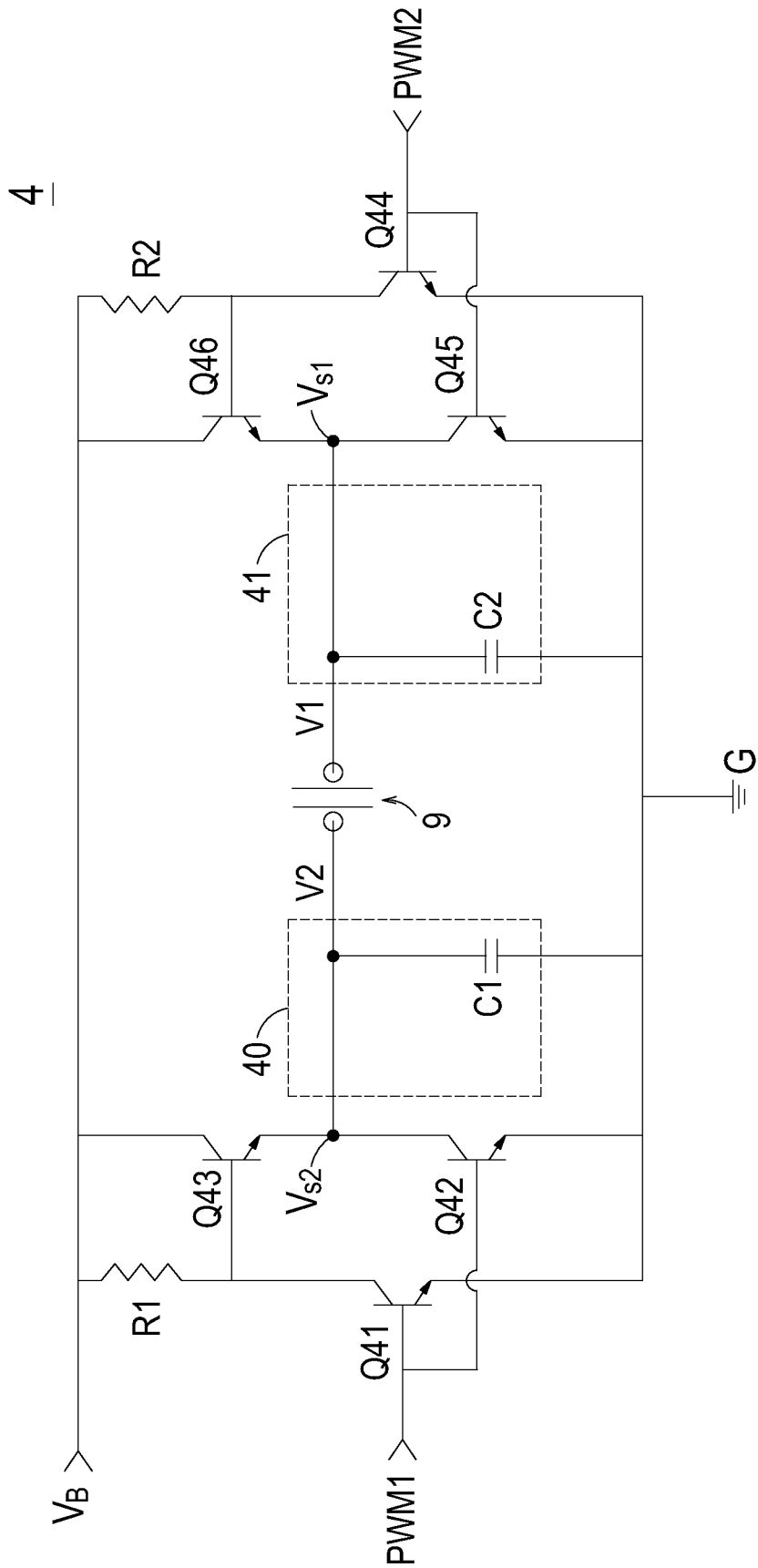
FIG. 6 shows an alternative example of the first filter and the second filter of FIG. 4A and FIG. 4B.

In alternative embodiments, the first filter 40 can include a first capacitor $C_1$ only, as shown in FIG. 6. In FIG. 6, the first capacitor $C_1$ is connected to a contact of the piezoelectric actuator 9, the current input terminal of the second transistor switch Q42, the current output terminal of the third transistor switch Q43, and the ground terminal G. The second filter 41 can include a second capacitor $C_2$ only, as shown in FIG. 6. In FIG. 6, the second capacitor $C_2$ is connected to another contact of the piezoelectric actuator 9, the current input terminal of the fifth transistor switch Q45, the current output terminal of the sixth transistor switch Q46, and the ground terminal G.

Figure 7A:
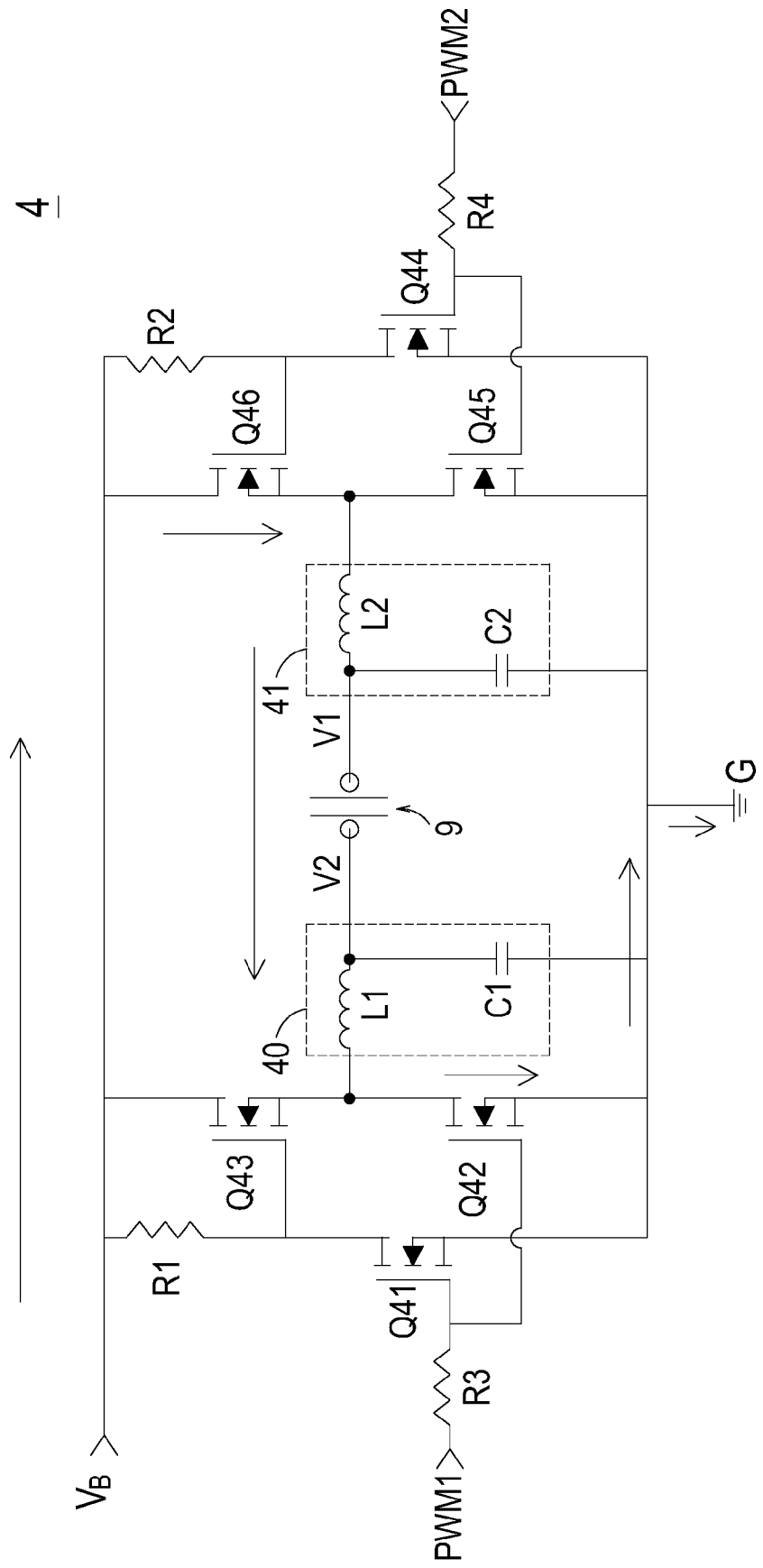
FIG. 7A and FIG. 7B show an alternative example of the polarity switching circuit of FIG. 4A and FIG. 4B.
Figure 7B:
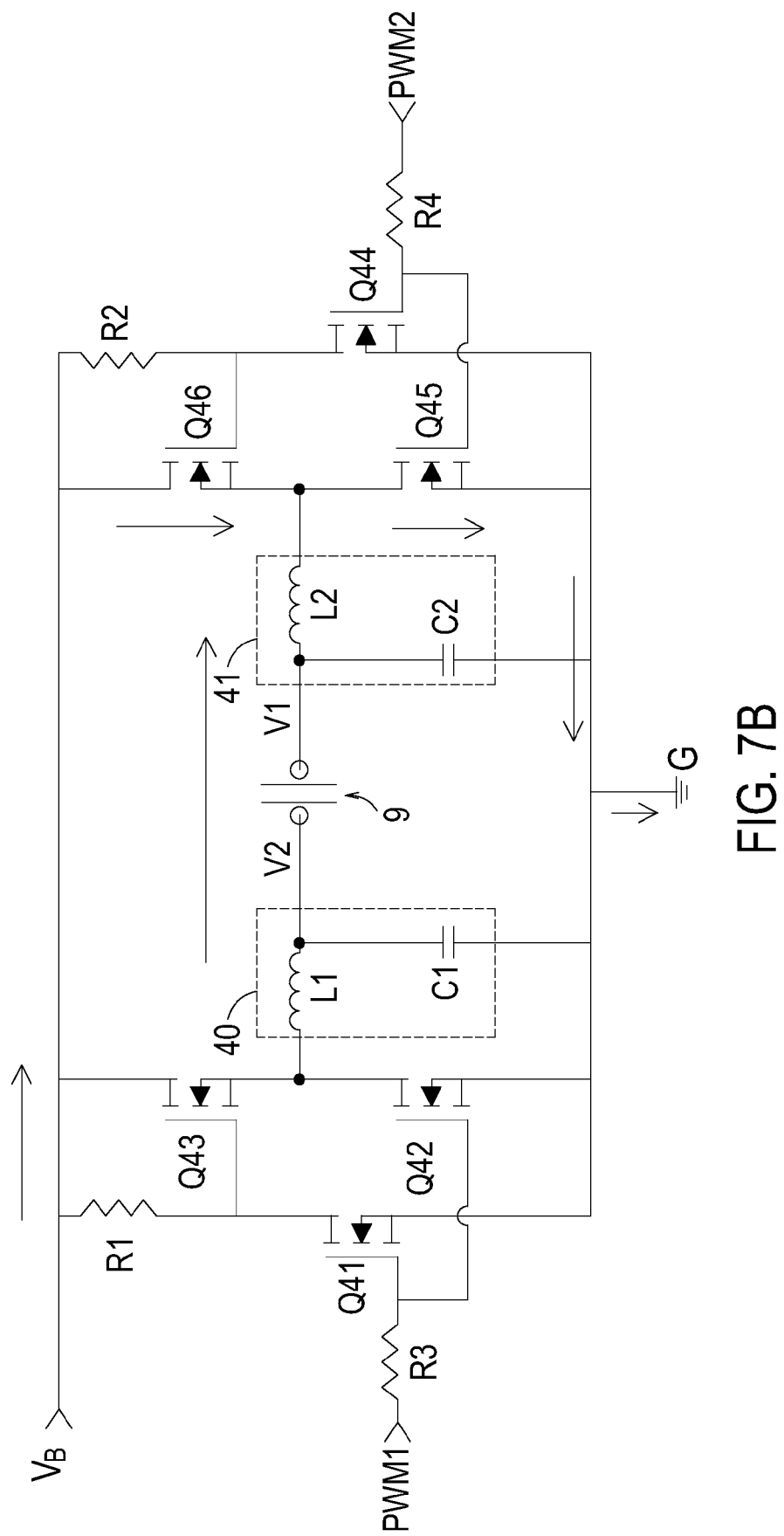

In alternative embodiments, the transistor switches Q41-Q46 can be implemented by NPN bipolar junction transistors (BJTs). Under this condition, the control terminal, the current input terminal, and the current output terminal of the transistor switches Q41-Q46 are constituted by the base, the collector, and the emitter, respectively. Nonetheless, in alternative embodiments, the transistor switches Q41-Q46 can be implemented by field-effect transistors (FETs), as shown in FIG. 7A and FIG. 7B. Under this condition, the control terminal, the current input terminal, and the current output terminal of the transistor switches Q41-Q46 are constituted by the gate, the source, and the drain, respectively. Furthermore, provided that the transistor switches Q41-Q46 are implemented by field-effect transistors (FETs), the polarity switching circuit 4 further includes a third current-limiting resistor R3 and a fourth current-limiting resistor R4. The third current-limiting resistor R3 is connected to the control terminal of the first transistor switch Q41 and the control terminal of the second transistor switch Q42. The fourth current-limiting resistor R4 is connected to the fourth transistor switch Q44 and the fifth transistor switch Q45. As the circuit topology and operation principle of the polarity switching circuit 12 of FIG. 7A and FIG. 7B are similar to those of the polarity switching circuit 12 of FIG. 4A and FIG. 4B, it is not intended to give details to the circuit topology and operation principle of the polarity switching circuit 4 of FIG. 7A and FIG. 7B herein.

Figure 8:
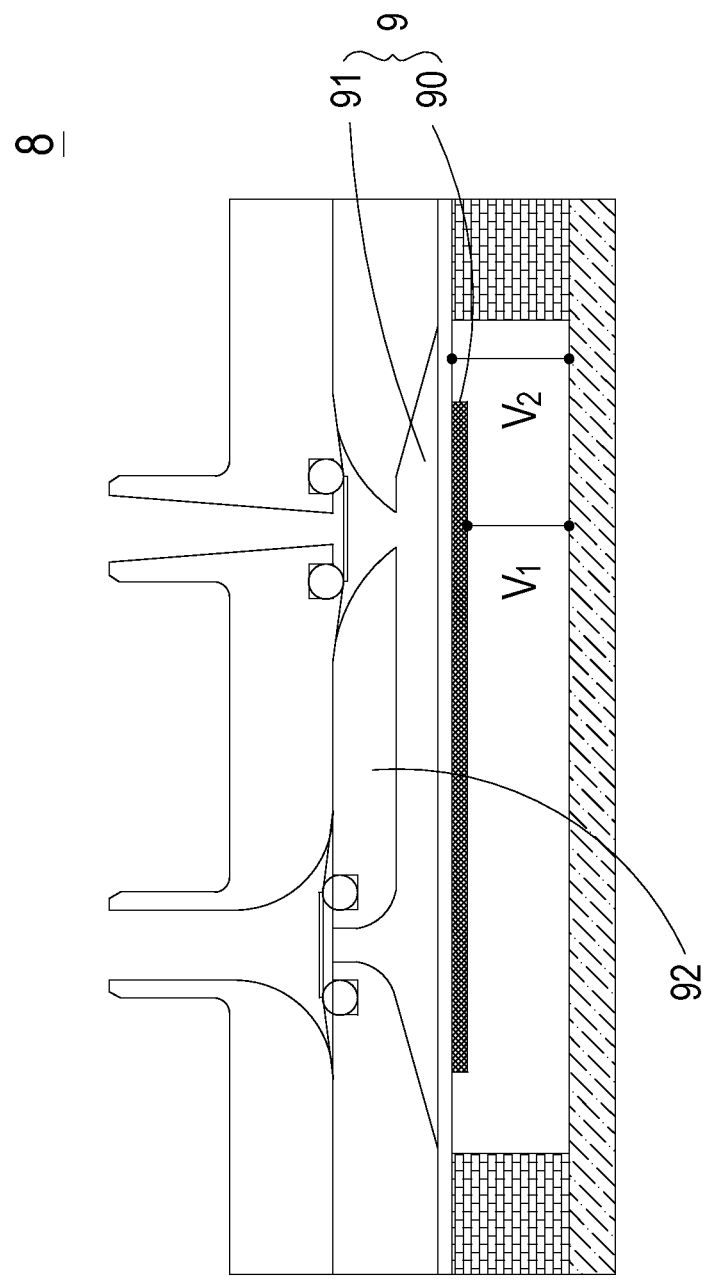
FIG. 8 is a structural view of a mechanical body incorporating the piezoelectric actuator of FIG. 4A.

Referring to FIG. 8, the structural view of a mechanical body incorporating the piezoelectric actuator of FIG. 4A is shown. In FIG. 8, the mechanical body may be a fluid transfer device 8 that is applicable to biomedical technology, computer technology, printing technology, or energy industry for transferring gas or liquid. The fluid transfer device 8 may be a pump in an inkjet printer for converting electric energy into mechanical energy. The piezoelectric actuator 9 includes an actuating piece 90 and a vibrating film 91 that are respectively connected to the output AC voltage $V_1$ and the output AC voltage $V_2$. The output AC voltage $V_1$ and the output AC voltage $V_2$ are used to drive the actuating piece 90 and the vibrating film 91 to operate repetitively to allow the pressure chamber 92 to be compressed or expanded, thereby enabling the fluid transfer device 8 to transfer fluid.

In conclusion, the inventive polarity switching circuit employs sixth transistor switches and two filters to output AC voltages with smoothed AC waveforms. Thus, the power loss of the piezoelectric actuator is reduced and the noise of the piezoelectric actuator is suppressed.

While the invention has been described in terms of what are presently considered to be the most practical and preferred embodiments, it is to be understood that the invention need not be restricted to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the invention which is defined by the appended claims.

What is claimed is:

1. A polarity switching circuit for converting a DC high voltage into an output AC voltage for driving a piezoelectric actuator, comprising:
    a first current-limiting resistor connected to the DC high voltage;
    a second current-limiting resistor connected to the DC high voltage;
    a first transistor switch having a control terminal receiving a first pulse-width modulating signal, a current input terminal connected to the first current-limiting resistor and the DC high voltage, and a current output terminal connected to a ground terminal directly;
    a second transistor switch having a control terminal receiving the first pulse-width modulating signal, a current input terminal, and a current output terminal connected to the ground terminal;
    a third transistor switch having a control terminal connected to the current input terminal of the first transistor switch and the first current-limiting resistor, a current input terminal connected to the DC high voltage, and a current output terminal connected to the current input terminal of the second transistor switch;

a fourth transistor switch having a control terminal receiving a second pulse-width modulating signal, a current input terminal connected to the DC high voltage through the second current-limiting resistor, and a current output terminal connected to the ground terminal directly;

a fifth transistor switch having a control terminal receiving the second pulse-width modulating signal, a current input terminal, and a current output terminal connected to the ground terminal;

a sixth transistor switch having a control terminal connected to the current input terminal of the fourth transistor switch and the second current-limiting resistor, a current input terminal connected to the DC high voltage, and a current output terminal connected to the current input terminal of the fifth transistor switch;

a first filter connected to the current input terminal of the second transistor switch, the current output terminal of the third transistor switch, a first contact of the piezoelectric actuator, and the ground terminal; and a second filter connected to the current input terminal of the fifth transistor switch, the current output terminal of the sixth transistor switch, a second contact of the piezoelectric actuator, and the ground terminal;

wherein when the first pulse-width modulating signal and the second pulse-width modulating signal are alternately and respectively switching between a high level and a low level, the first filter and the second filter are configured to filter the output AC voltage into a smoothed AC waveform, thereby providing an output AC voltage with a smoothed waveform for the piezoelectric actuator.

2. The polarity switching circuit according to claim 1 wherein when the first pulse-width modulating signal is switching between a high level and a low level, the second pulse-width modulating signal is at a low level, and when the second pulse-width modulating signal is switching between a high level and a low level, the first pulse-width modulating signal is at a low level.

3. The polarity switching circuit according to claim 1 wherein the first pulse-width modulating signal and the second pulse-width modulating signal are set to drift from a high-frequency band to a low-frequency band and then to a high-frequency band.

4. The polarity switching circuit according to claim 1 wherein the first filter includes:

a first inductor connected to the first contact of the piezoelectric actuator, the current input terminal of the second transistor switch, and the current output terminal of the third transistor switch; and a first capacitor connected to the first contact of the piezoelectric actuator, the first inductor, and the ground terminal.

5. The polarity switching circuit according to claim 1 wherein the second filter includes:

a second inductor connected to the second contact of the piezoelectric actuator, the current input terminal of the fifth transistor switch, and the current output terminal of the sixth transistor switch; and a second capacitor connected to the second contact of the piezoelectric actuator, the second inductor, and the ground terminal.

6. The polarity switching circuit according to claim 1 wherein the first filter includes a first capacitor connected to the first contact of the piezoelectric actuator, the current input terminal of the second transistor switch, the current output terminal of the third transistor switch and the ground terminal, and the second filter includes a second capacitor connected to the second contact of the piezoelectric actuator, the current input terminal of the fifth transistor switch, the current output terminal of the sixth transistor switch and the ground terminal.

7. The polarity switching circuit according to claim 1 wherein the output AC voltage with the smoothed waveform reaches a first fractional value of a maximum voltage linearly within a first time period after the polarity switching circuit starts operating, and smoothly bobs up and reaches the maximum voltage within a first predetermined time period; and then the output AC voltage with the smoothed waveform remains flat within a second time period and smoothly declines and reaches a second fractional value of the maximum voltage linearly within a second predetermined time period; and then the output AC voltage drops to zero linearly.

* * * * *